United States Patent [19]

Erwin et al.

[11] Patent Number: 4,509,360
[45] Date of Patent: Apr. 9, 1985

[54] ON-LINE MEASUREMENT OF FLUID MIXTURES

[75] Inventors: Lewis Erwin, Winchester, Mass.; Jeffrey L. Dohner, Fort Wayne, Ind.

[73] Assignee: Massachusetts Institute of Technology, Cambridge, Mass.

[21] Appl. No.: 508,217

[22] Filed: Jun. 24, 1983

[51] Int. Cl.³ .................................. G01N 29/00
[52] U.S. Cl. ........................... 73/61 R; 73/599; 73/642; 73/644
[58] Field of Search ............... 73/599, 642, 61 R, 644

[56] References Cited

U.S. PATENT DOCUMENTS

| | | | |
|---|---|---|---|
| 2,697,936 | 12/1954 | Farrow | 73/644 |
| 3,774,717 | 11/1973 | Chodorow | 73/599 |
| 3,908,446 | 9/1975 | Mruk | 73/644 |
| 4,297,886 | 11/1981 | Anikeev et al. | 73/644 |
| 4,327,587 | 5/1982 | Docekal et al. | 73/597 |
| 4,346,599 | 8/1982 | McLaughlin et al. | 73/597 |
| 4,412,451 | 11/1983 | Uusitalo | 73/599 |
| 4,437,332 | 3/1984 | Pittaro | 73/644 |

Primary Examiner—Howard A. Birmiel
Attorney, Agent, or Firm—Arthur A. Smith, Jr.; Thomas J. Engellenner

[57] ABSTRACT

An apparatus and method for measuring particle agglomeration or dispersion in fluid mixtures, such as polymer melts, resides in a piezoelectric transducer, a spherical fused quartz lens, and a fluid housing. A repetitive, broadband, ultrasonic wave is produced by the transducer and is sent into the lens, which also serves to isolate the transducer from the mixture. The ultrasonic wave meets a spherical dimple at the end of the lens which focuses a portion of it into a diffraction limited spot or "interrogation zone". Since the intensity of the wave is large in the interrogation zone, small changes in the impedance of the fluid in this zone, caused by passing agglomerates, will cause large fluctuations in the intensity of the back scattered wave, which is monitored by the transducer between pulses and displayed by associated electronic elements.

23 Claims, 10 Drawing Figures

CLEAN POLYETHYLENE MELT

POLYETHYLENE GLASS 20% BY WEIGHT
(10 - 55 um)

POLYETHYLENE GLASS 20% BY WEIGHT
(44 - 74 um)

POLYETHYLENE GLASS 20% BY WEIGHT
(74-149 um)

POLYETHYLENE CARBON BLACK (2% BY WEIGHT)

POLYETHYLENE CARBON BLACK (2% BY WEIGHT)
LIGHT MICROGRAPH

POLYETHYLENE & POLYSTYRENE
(10% BY WEIGHT)

⟵⟶ 150 um

POLYETHYLENE & POLYSTRYRENE
(10% BY WEIGHT)
LIGHT MICROGRAPH

ON-LINE MEASUREMENT OF FLUID MIXTURES

TECHNICAL FIELD

This invention relates to polymer processing and, generally, to measurement of particle aggolmeration or dispersion in fluids.

BACKGROUND OF THE INVENTION

Attention is directed to a Master of Science thesis by one of the inventors, J. L. Dohner, entitled "An On-Line Measurement of Particle Dispersion in Polymer Melts" submitted to Massachusetts Institute of Technology, which will become available to the public upon the filing of this application. This thesis is incorporated herein by reference.

In the plastics industry, additives are often mixed with polymers to produce a plastic with a desired set of material properties. For example, carbon black is mixed with polyethylene to protect the polyethylene from ultraviolet radiation. Titanium dioxide is used with many polymers to act as an opacifier, and polypropylene and polyethylene are mixed to produce an inexpensive high-impact material.

A problem that arises in polymer processing is that the material properties of the final batch are not only a function of the materials being mixed but also a function of the "quality of mixing" in the batch. Two different batches of the same material will have a different set of properties depending on the degree of mixing in each. The elastic modulus, the rate of die swell, the viscosity of the melt, and the cyclic life of the product are a few of the properties affected by the degree of dispersion during processing:

In order for these properties to meet given standards, the melt should be mixed to a given degree. Nevertheless, as the "quality of mixing" improves, the amount of power required to further improve mixing in the melt increases. Thus, the goal of most research in the field of fluid mixing has been to move the state of a melt from an unmixed state to a given state of mixing with a mineral amount of work. The desired state of mixing should not be exceeded.

If it were possible to measure the degree of mixing at the exit of a piece of mixing machinery while mixing was occurring, useful evaluation of the performance of that mixing machinery could be made. There exists a need for an apparatus that would avoid trial and error methods of molding plastic or ceramic parts from fluid precursors. Such a system would also eliminate the time-consuming methods of microscopy presently used to measure mixing in polymer melts and would create a foundation for closed-loop fluid mixing systems for many applications.

SUMMARY OF THE INVENTION

We have devised a simple, effective on-line apparatus for analyzing the components in a fluid mixture employing a housing with a fluid passageway and a focusing surface within the housing. The focusing surface is coupled to a source of ultrasonic wave energy, such as an ultrasonic pulse. Unmixed or agglomerated particles in the fluid stream can be detected by measuring changes in the scattered wave. In a simple embodiment the source of wave energy and the detector both are incorporated into a single device.

In one preferred embodiment our apparatus consists of a piezoelectric transducer, a spherical fused quartz lens, and a fluid housing. A repetitive, broadband, ultrasonic wave is produced by the contact transducer and is sent into the cylindrical section of the lens. The ultrasonic wave meets a spherical dimple at the end of the lens which focuses a portion of it into a diffraction limited spot or "interrogation zone". Since the intensity of the wave is large in the interrogation zone, small changes in the impedance of the fluid in this zone, caused by passing agglomerates, will cause large fluctuations in the intensity of back scattered sound. This back scattered sound travels from the spot back to the piezoelectric transducer. At the piezoelectric transducer, the back scattered wave is changed into a voltage which is relayed to accompanying electronics.

In another aspect of our invention a pulser/receiver supplies the repetitive voltage required to drive the piezoelectric transducer while intermittently receiving back scattering voltage information. By using the pulser/receiver's internal functions, an analog signal is produced which is proportional to the amplitude of voltage fluctuations caused by back scattering in the interrogation zone. The analog signal can be digitized for data manipulation. By relating the peak values of the digitized output to the size of the agglomerates in the zone, a plot of the number of aglomerates versus particle size can be obtained. The pressure and temperature of the fluid are also monitored in order to detect changes in sound speed and spot size.

We have found that for most applications, agglomerates or aggregates can be detected using interrogating wavelengths between 10 and 1000 microns, and preferably between 100 and 1000 microns, generated by a transducer vibrating in the 1.0 and 10.0 megahertz range. In general, the wavelength of sound should be chosen such that the sound waves are scattered by large agglomerates but not by smaller ones. In the fluid, there will always be a large number of small aggregates (for example, less than a micron in diameter) and a fewer number of large agglomerates (greater than 10 microns in diameter). The smaller aggregates represent regions of enhanced mixing. The larger agglomerates represent regions of poor mixing. Either of these regions may be used to represent the degree of mixing in the fluid, however, if small particles are detected, the fluid's attenuation will be relatively large. In our experiments, we have found that a 667 micron wavelength minimized the fluid's attenuation while allowing for the detection of particles greater than 10 microns in diameter, although it should be clear that the wavelength can be varied and resolution will generally be proportional to the wavelength.

Our invention will next be described below in connection with one preferred embdiment used in connection with polymer processing; however, it should be clear that various changes, modifications and other applications can be devised without departing from the spirit and scope of our invention. For example, a wide variety of fluid mixtures may be analyzed with our device, such as paints, pharmaceuticals, and rubbers as well as plastics. The mixtures may be conductive or non-conductive and may be opaque or transparent without affecting our method. The additives may include $TiO_2$, $CaCO_3$, magnetic particles, carbon black, metallic particles, pigments, and the like. Specific polymers which can be analyzed with our device include polyethylene, polypropylene and polystyrene, nylons, polyesters and elastomers.

The apparatus and method can also find applications in medical use analyzing, for example, the clotting or agglomeration of particles in a blood stream. Our method can be useful in extracorporeal blood pumps and filters, dialysis machines and heart-lung machines. Similarly, the invention can find use in the beverage industry to detect the degree of carbonation in beverages, or more generally, the size and density of gas bubbles in a liquid.

DESCRIPTION OF PREFERRED EMBODIMENTS

Figure 1:
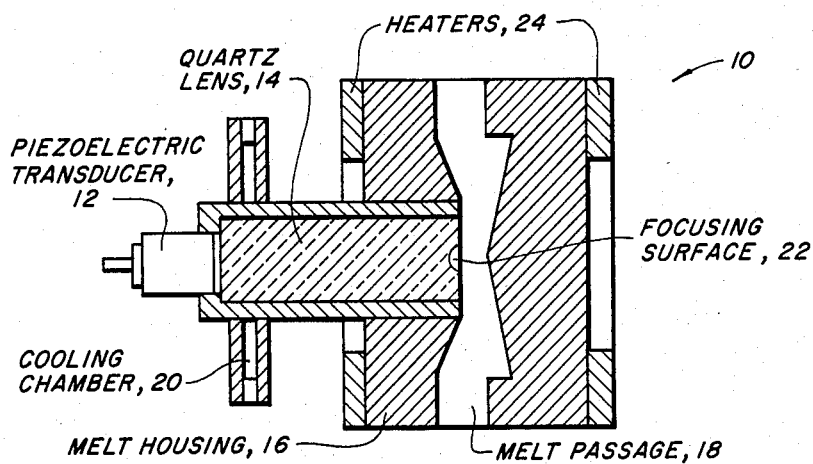
FIG. 1 is an isometric view of the analyzing apparatus of this invention.
Figure 1A:
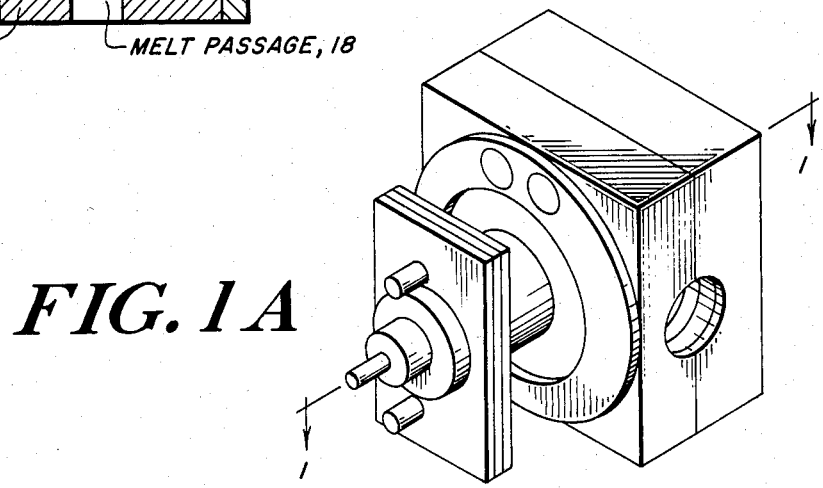
FIG. 1a is a cross-sectional view at plane A—A.

In FIG. 1 our apparatus 10 is shown consisting of a piezoelectric transducer 12 (Panametrics, 2.25 Mhz, 0.5 in dia. dimple, 0.125 in depth), a fluid housing 16 having a fluid passageway 18 and a cooling chamber 20 connected to the transducer 12. The pyrex lens 14 acts as a delay line as well as a focusing device. It is cooled on one end by a cooling chamber 20 and heated on the other by the fluid. The fluid is forced through its housing parallel to the face of the lens. Heaters 24 may be incorporated in the housing 15 to insure that the fluid composition is not charged during analysis. The piezoelectric transducer is driven by a pulser-receiver system and output is stored on a digital scope, as discussion below in connection with FIG. 2.

In operation an acoustical wave pulse, generated by the piezoelectric transducer 12, travels the length of the lens 14. At the lens' end, it strikes a spherical dimple 22. The wave then undergoes mode conversions where a fraction of its energy is reflected back into the lens 14 as a shear and longitudinal wave, and a fraction of its energy is transmitted into the fluid as a shear and longitudinal wave. The fraction of the wave that is reflected back into the lens is allowed to reverberate. Each time it strikes the fluid-lens interface, additional energy is transferred into the fluid. That portion of the wave that is transmitted will form two diffraction limited spots. One spot will be due to the shear wave, and another spot will be due to the longitudinal wave (double imaging). The shear wave's spot will produce back scattering dominated by shear waves. The longitudinal wave's spot will produce back scattering dominated by longitudinal waves. For most plastic fluids, the attenuation of shear waves is much greater than the attenuation of longitudinal waves. Thus, for a given frequency and geometry, when the longitudinal wave's attenuation is large, the shear wave's spot may be neglected.

Figure 2:
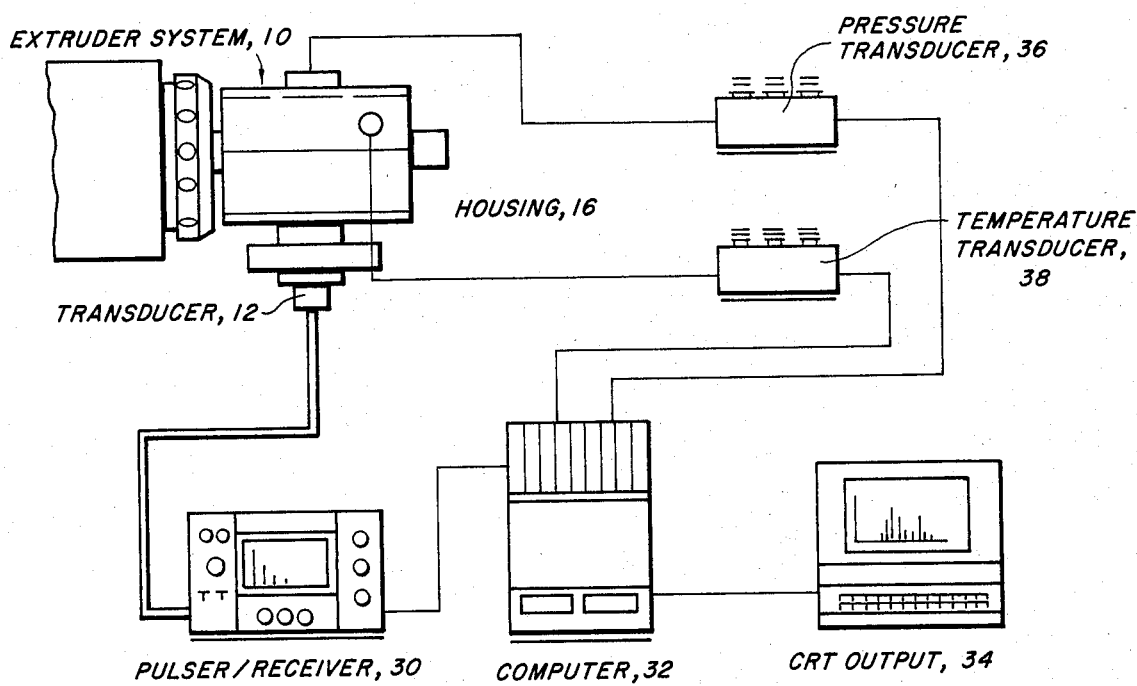
FIG. 2 is a schematic diagram of the system electronics supporting our analyzing apparatus.

In FIG. 2 the system electronics are shown schematically consisting of transducer 12, pulser/receiver 30 (USM2 flaw detector), logic unit 32, and display unit 34 (VT 100). In the preferred embodiment pressure sensor 36 and temperature sensor 34 may also be connected to the housing 16 to provide the logic unit 32 with data on the fluid's pressure and temperature (which can affect the analysis).

The invention will next be described in connection with certain working examples.

EXAMPLE I

Figure 3:
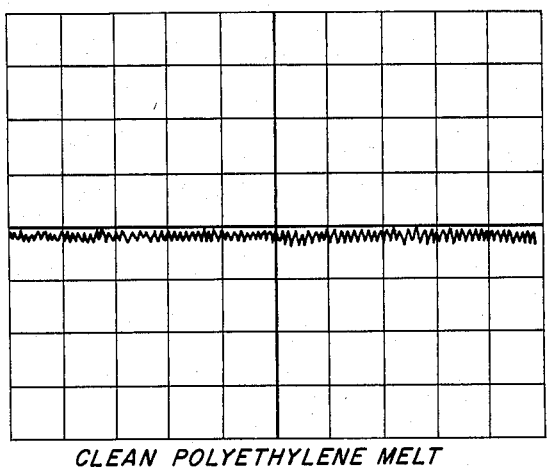
FIG. 3 is a photograph of the output of our apparatus analyzing clean polyethylene.

In order to determine the system's resolution and background noise, a clean fluid melt, consisting of linear polyethylene mixed with 20% by weight calcium carbonate, was run through the apparatus. The output shown in the following figures was taken from the gated peak signal of the pulser/receiver and displayed on a 7854 Tektronix Oscilloscope. Digitizing and data manipulation occurs in the logic unit and is not seen. The diameter of the calcium carbonate particles were all below a micron. The gain on the receiver was 20 dB, the width of the gate was 0.1 microseconds (150 microns in water), and the vertical scale of the scope was set 0.1 volts per division. These settings applied for all experiments. The noise level of this system was less than 30 millivolts peak to peak, as shown in FIG. 3.

EXAMPLE II

In a second set of experiments, dispersions of polyethylene and glass beads were tested. Each mixture contained glass beads of a different size range. These mixtures consisted of a clean melt mixed with 20% by weight glass. They were tumbled mixed.

Figure 4A:
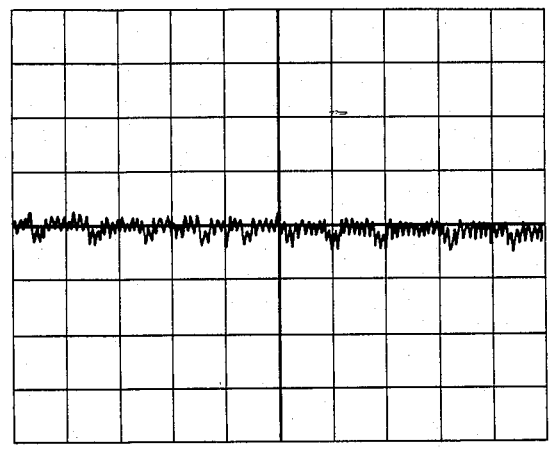
FIGS. 4a–4c are photographs of the output of the apparatus analyzing polyethylene mixed with glass beads of varying sizes.
Figure 4B:
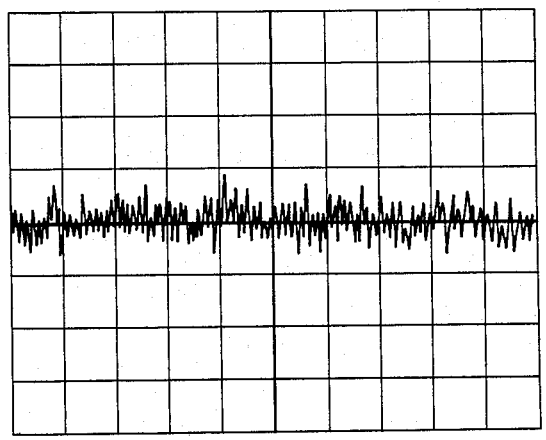
Figure 4C:
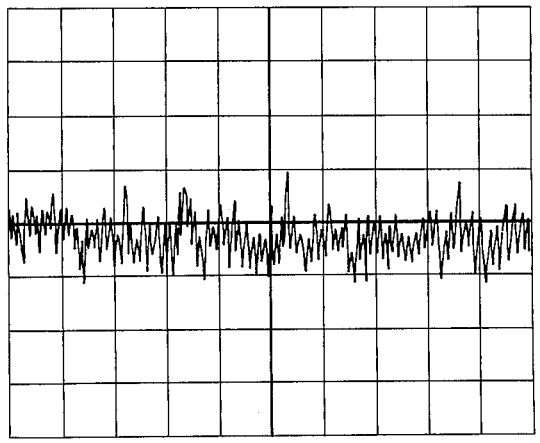

For the size range between 10 to 148 microns, the peak to peak value of the output increases as the size of the particles in the melt increase, thus, a calibration of particle size versus output voltage was demonstrated. The results of analyzing three mixtures containing varying sized beads are shown in FIGS. 4a, 4b, and 4c.

EXAMPLE III

Figure 5A:
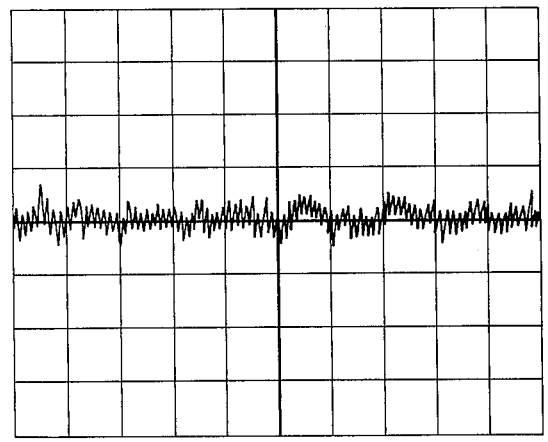
FIG. 5a is a photograph of the output of our apparatus analyzing a polyethylene and carbon black mixture.
Figure 5B:
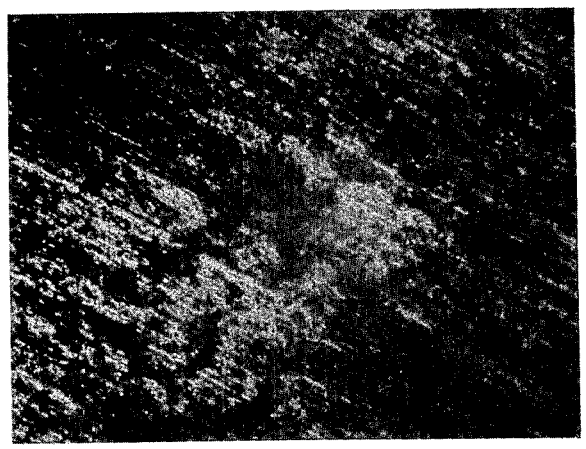
FIG. 5b is a micrograph of the mixture.

Mixtures of polyethylene and carbon black were tested. Again, the polyethylene was linear polyethylene with a 20% by weight background of calcium carbonate. The calcium carbonate was below a micron in particle diameter. The carbon black was 2% by weight of the total mixture. The polyethylene and carbon black were tumbled mixed prior to extrusion. As seen in the output in FIG. 5 and the micrograph in FIG. 5b, fluctuations in this mixture's properties were detectable. The peak to peak voltage of this output was 70 millivolts. This was 40 millivolts above the background noise.

EXAMPLE IV

Figure 6A:
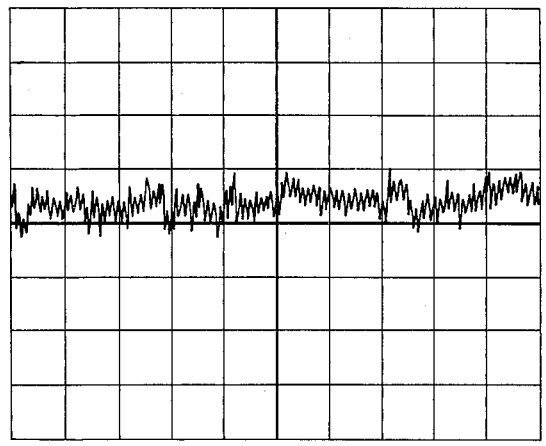
FIG. 6a is a photograph of the output of our apparatus analyzing a polyethylene-polystyrene mixture.
Figure 6B:
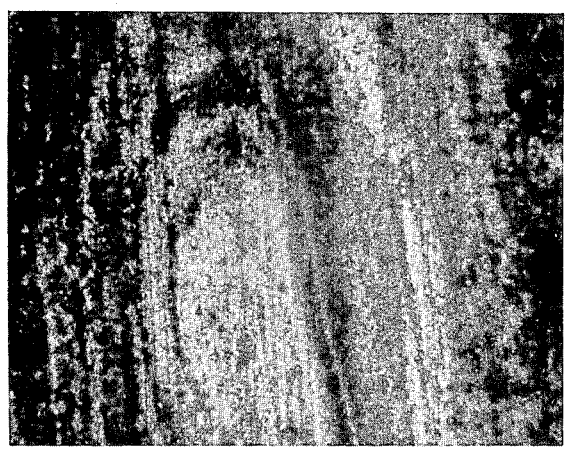
FIG. 6b is a micrograph of the mixture.

A polyethylene and polystyrene mixture was tested next. Again, the polyethylene was linear polyethylene with the 20% by weight calcium carbonate background. The polystyrene was 10% by weight of the total mixture. As seen in the output in FIG. 6a and the micrograph in FIG. 6b, fluctuations in this mixture's properties were also detectable. The peak to peak voltage of this output was 112 millivolts. This was 96 millivolts above the background noise.

What we claim is:

1. An apparatus for determining the degree of mixing of components in a fluid mixture, the apparatus comprising:
   (a) a housing having a passageway through which the fluid mixture to be analyzed passes;

(b) a source of wave energy;

(c) a focusing surface coupled to the source of wave energy transmitting the wave energy into the fluid mixture and focusing the wave energy in the passageway in an interrogation zone within the passageway such that changes in the impedance of the fluid mixture caused by unmixed components within the zone will cause fluctuations in the intensity of backscattered wave energy; and (d) a detector means also coupled to the fluid mixture within the passageway for detecting a portion of the focused wave energy back scattered by the components and thereby determining the dispersion of components in the fluid mixture by measuring fluctuations in the intensity of the backscattered portion of the wave energy.

2. The apparatus of claim 1 wherein the apparatus further comprises a wave guide coupling means for mechanically coupling the source of wave energy and the detector means, to the fluid mixture while providing thermal isolation therebetween.

3. The apparatus of claim 2 wherein the wave guide coupling means is a cylindrical wave guide.

4. The apparatus of claim 3 wherein the wave guide is a quartz lens.

5. The apparatus of claim 3 wherein the cylindrical wave guide is a glass lens.

6. The apparatus of claim 3 wherein the cylindrical wave guide is a metal lens.

7. The apparatus of claim 1 wherein the source of wave energy and the detector means are formed as an integral unit.

8. The apparatus of claim 7 wherein the integral unit is a piezoelectric transducer.

9. The apparatus of claim 8 wherein the transducer is an ultrasonic transducer.

10. The apparatus of claim 1 wherein the apparatus further comprises a heater disposed within the housing to maintain the fluid mixture at a predetermined temperature.

11. The apparatus of claim 1 wherein the apparatus further comprises a cooling unit disposed about the detector means to maintain the detector means at a predetermined temperature.

12. The apparatus of claim 1 wherein the apparatus further comprises a temperature sensor disposed within the housing to monitor the temperature of the fluid mixture.

13. The apparatus of claim 1 wherein the apparatus further comprises a pressure sensor disposed within the housing to monitor the pressure of the fluid mixture.

14. The apparatus of claim 1 wherein the housing forms an integral part of a processing system for the fluid mixture.

15. The apparatus of claim 1 wherein the source of wave energy is a source of acoustic wave energy.

16. The apparatus of claim 1 wherein the source of wave energy ia a source of ultrasonic wave energy.

17. The apparatus of claim 1 wherein the focusing surface is a surface with radial symmetry.

18. The apparatus of claim 17 wherein the focusing surface is a cylindrical surface.

19. The apparatus of claim 17 wherein the focusing surface is a spherical dimple.

20. The apparatus of claim 1 wherein the source of wave energy is an ultrasonic transducer operating at a wave length from about 10 microns to about 1000 microns.

21. The apparatus of claim 20 wherein the operating wave length ranges from about 100 microns to about 1000 microns.

22. An apparatus for determining the degree of mixing of components in a fluid mixture, the apparatus comprising:

(a) a housing having a passageway through which the fluid mixture to be analyzed passes;

(b) a piezoelectric transducer capable of generating a train of acoustic pulses and receiving backscattered waves between pulses;

(c) a cylindrical quartz lens to mechanically couple the transducer to the mixture, while providing thermal isolation therebetween; and (d) a spherically-dimpled focusing surface located on the lens and within the housing, capable of focusing the ultrasonic wave energy transmitted by the lens to the mixture in an interrogation zone within the passageway such that changes in the impedance of the fluid mixture caused by unmixed components within the zone will cause fluctuations in the intensity of backscattered wave energy, whereby the dispersion of components in the liquid mixture is determined by the transducer by measuring fluctuations in the intensity of the backscattered wave energy.

23. A method of detecting the presence of agglomerates in a fluid mixture, the method comprising:

(a) focusing a repetitive broadband ultrasonic wave in an interrogation zone through which the fluid mixture passes such that changes in the impedance of the fluid mixture within the zone, caused by passing agglomerates, will cause fluctuations in the intensity of backscattered waves; through which the fluid mixture passes; and (b) measuring changes in the intensity of the backscattered wave caused by passing agglomerates.

* * * * *